United States Patent [19]

Melker et al.

[11] Patent Number: 5,599,303
[45] Date of Patent: Feb. 4, 1997

[54] IV ADMINISTRATION APPARATUS

[76] Inventors: Richard Melker, 6101 NW. 19th Pl., Gainesville, Fla. 32605; Eric J. Hulsman, 1006 Countryside La., Smyrna, Ga. 30080; Brad D. Wellington, 887 Westmont Dr., Asheboro, N.C. 27203

[21] Appl. No.: 344,829

[22] Filed: Nov. 21, 1994

[51] Int. Cl.$^6$ .................................................. A61M 5/14
[52] U.S. Cl. ................................................ 604/80; 604/246
[58] Field of Search ........................... 604/80, 9, 30, 604/65, 81, 122, 246, 251, 253, 254, 258, 260, 407; 73/861; 116/273, 264, 274, 275

[56] References Cited

U.S. PATENT DOCUMENTS

| | | | |
|---|---|---|---|
| 1,574,460 | 2/1926 | Williamson | 116/275 |
| 3,251,335 | 5/1966 | Dannevik | 116/275 |
| 3,797,480 | 3/1974 | Williams | 128/726 |
| 3,949,737 | 4/1976 | Nielsen | 128/726 |
| 4,187,847 | 2/1980 | Loeser | 604/246 |
| 4,287,775 | 9/1981 | Hutton | 128/726 |
| 4,389,901 | 6/1983 | Lake . | |
| 4,694,161 | 9/1987 | Sackett . | |
| 4,801,106 | 1/1989 | Kawakami et al. | 242/159 |
| 5,059,173 | 10/1991 | Sacco . | |
| 5,343,763 | 9/1994 | Nielsen et al. . | |
| 5,370,683 | 12/1994 | Fontaine | 606/198 |

Primary Examiner—Corrine M. McDermott
Assistant Examiner—N. Kent Gring
Attorney, Agent, or Firm—Saliwanchik & Saliwanchik

[57] ABSTRACT

The subject invention is a novel apparatus for the administration of intravenous fluids. The invention is particularly well suited for accurately and efficiently administering intravenous fluids over a wide range of flow rates. Disclosed is an intravenous fluid administration apparatus having at lease one flow line capable of administering fluid at high flow rates and comprising an airless, dripless, fluid monitoring chamber. A preferred embodiment comprises a main flow line which diverges into at least two flow limbs, where one flow limb is a low-flow limb and another flow limb is a high-flow limb, each having separate flow indicators, and with the flow limbs typically converging into a common tube for fluid delivery to the patient. The subject invention also discloses a novel flow meter, which is particularly well suited for measuring and indicating flow rates over a wide range, without the introduction of air bubbles into the fluid flow being measured. The novel flow meter of the subject invention comprises an elastic displaceable member in a housing, whereby the relative position of the displaceable member, as effected by the amount of force exerted on the displaceable member by the fluid being measured, indicates the flow rate of the fluid.

21 Claims, 4 Drawing Sheets

IV ADMINISTRATION APPARATUS

BACKGROUND OF THE INVENTION

To improve health care, there has been considerable effort with regard to the administration of intravenous (IV) fluids. Both controllers and pumps have been developed for delivering metered amounts of IV fluid to the patient.

A variety of systems have been utilized to supply or administer various liquids such as blood, nutrient or pharmaceutical solutions, and so on to human and animal patients. When intravenous administration of liquids is desired, the most commonly used apparatus to achieve such administration comprises a container for the liquid to be administered, a tube connected to the container, and a hollow needle or plastic catheter at the end of the tube to be introduced into the patient's vein, with the fluid flowing under gravity out of the container through the tube. Frequently, some manually operated mechanical device is provided, such as an adjustable clamp, for controlling the rate of flow from the storage container into the patient by varying the resistance in the tube to the fluid flow. The actual flow rate is dependent in addition on the pressure of the fluid passing through the tube, which is in turn a function of the differential in height between the level of liquid in the container and the point of administration to the patient, or externally applied pressure sources.

In the above described gravity systems, the rate of flow into the patient, i.e., the quantity of liquid administered to the patient per unit time, is subject to substantial fluctuation. Even though a transparent drip chamber is frequently provided in these gravity systems whereby the rate of drops flowing from the container into the tube can be observed and measured per unit time, the actual rate of fluid outflow from the administering system and into the patient is quite variable. Variation in rate of flow can be the result of different degrees of resistance in the system from differences in fluid density and viscosity, or even of variations in back pressure exerted against the fluid flow from changes in the patient's blood pressure. Moreover, the volume of the drips is neither constant nor precise. Accordingly, the number of drops is not a precise indication of flow rate. Such fluctuations in flow rate experienced with the widely-used gravity systems can lead to undesirable consequences.

Improved systems for the administration of liquids to patients have been proposed in the prior art to overcome some of the drawbacks of the gravity-based systems. These improved systems are essentially of two types. In the first type, an attempt is made to provide means for controlling the resistance to flow through the system in a more accurate and refined manner than the standard adjustable clamp which constricts the tube through which the fluid flows. For example, mechanical variable resistance devices have been interposed in the fluid flow line which do not require constriction or crimping of the tubing but instead provide flow-through apertures of various sizes, depending on the degree of resistance desired. A second type of improved prior art device attempts to regulate by a variety of means the pressure head of the fluid flowing from the container or bag.

One common apparatus comprises a stand from which is suspended a liquid reservoir, e.g., in the form of a bag made of plastic material. Liquid is fed under gravity from the reservoir to the patient via a tube which is formed with a drip chamber. A clamp is provided downstream of the drip chamber, and can be adjusted so as to vary the flow restriction caused by the clamp, and thus vary the flow rate. The flow rate is estimated by counting the rate of drips in the drip chamber.

Setting up the apparatus is time consuming, and requires priming of the drip chamber which, if not done carefully, could result in problems such as air bubbles in the liquid being delivered to the patient. Also, in some circumstances the apparatus is not sufficiently accurate. In these cases, the tendency is to use a peristaltic pump for liquid infusion. This gives highly accurate results, but is very expensive, and requires special calibrated tubing which must be changed daily.

Another known form of apparatus uses a sensor for counting drips and a regulator to control flow in response to the drip rate. Commonly this is accomplished by means of a disposable cassette. This also has the problem of the drip chamber cassettes making the cost of usage high, and has a fairly high current consumption.

The rate at which an intravenous fluid is to be administered to a patient depends upon such factors as the particular kind of operation to be performed on the patient, the seriousness of the patient's illness or injury, or the patient's pulse rate, blood pressure or heart condition. For example, 500 milliliters of intravenous fluid are usually administered in 1 to 3 hours, but are sometimes administered in 4 or 5 hours.

During most normal procedures, IV fluids are administered continuously over extended periods of time at relatively low flow rates. Oftentimes, however, a situation, such as the need for surgery or fluid resuscitation, will arise where a continuous low flow fluid path will not satisfy the needs of the patient. Under these conditions, the low-flow administration set-up is removed and replaced with a high-flow set-up. When the patient's special needs are satisfied, the high-flow administration set-up is removed and once against replaced with a new low-flow set-up.

This repeated setting up and taking down of the IV system is a time consuming procedure which wastes substantial amounts of health care time. The loss of time, particularly during emergency procedures, can increase the patient's risk factor. In fight of the fact that an IV administration set-up can be used only once, the use of multiple set-ups during a single procedure can be relatively costly. Further, inventory levels must take into account the need for multiple set-ups, and multiple set-ups means multiple disposal as well. Frequent IV starts increase the risk of infection to the patient. Thus, any reduction in the number of starts and set-ups used per patient will be of an immediate benefit to both patient and health care workers alike.

Presently available IV sets provide either low-flow controlled flow rates, or high flow rates that are poorly controlled. At present, the end user must switch back and forth between these two types of sets. High flow rate sets can be dangerous, as it is difficult to control the flow rate when low rates are desirable. In addition, it is difficult to accurately monitor the flow rate under such conditions.

A variety of fluid flow meters have been described. See, for example, U.S. Pat. No. 4,389,901, and references cited therein.

Sacco (U.S. Pat. No. 5,059,173) has disclosed a dual chamber IV set, one chamber having a "mini" drip, and one a "maxi" drip. Thus Sacco envisions two drip chambers: no chamber is "dripless". While Sacco discloses a "high-flow" limb, he is not addressing flow rates necessary for volume resuscitation, but rather flow rates that are merely higher than available with a "mini" drip device. At flow rates necessary for volume resuscitation, the drip chamber of the Sacco "high-flow" limb would be a source of bubbles which could lead to air emboli. When fluid is forced through the "high-flow" limb of the Sacco device and into the "maxi" drip chamber, the fluid is entering the chamber as a high-speed jet. A Venturi effect results, causing air to entrain in the fluid stream, which creates great turbulence and aeration in the chamber and frothing of the liquid. A train of air bubbles can thereby be drawn into the administration line and then into the flow device and on into the patient. Such bubbles are a fife-threatening hazard to the patient. In contrast, the subject invention has a "dripless" chamber which eliminates the possibility of air emboli. Also, the subject invention uses a flow indicator component rather than a drip chamber to indicate flow rate.

BRIEF SUMMARY OF THE INVENTION

The subject invention addresses a number of objects: to improve flow paths used to administer IV fluids to a patient; to conserve valuable health care time when administering fluids; to lessen a patient's risk when undergoing medical procedures involving the administration of IV fluids; to reduce the amount of equipment required to administer IV fluids to patients; to reduce the cost involved in administering IV fluids to a patient; to reduce the amount of inventory that must be kept on hand by a health care facility; to reduce the amount of IV equipment that must be disposed of by health care facilities; to reduce the number of IV changes to safely satisfy a patient's needs; to provide a flow rate sensing device which can be incorporated into systems for monitoring flow rate or coordinating flow rate over a range from very low to very high flow rates; to reduce the risk of air emboli during high flow rate infusions; to provide a device of the character described which comprises relatively few and simple parts, is inexpensive and easy to manufacture, and can readily be made disposable so that a new, sterile device can be utilized for each patient; and to provide a device of the character described which is portable, non-electric, and light in weight. These and other objects and advantages of the subject invention will become evident from the summary and description that follows.

The subject invention concerns a new apparatus for the accurate and efficient administration and measurement of fluid over a range of flow rates. Specifically exemplified herein is the use of a novel flow meter to measure the flow rate in a novel intravenous fluid delivery system. The subject invention is particularly advantageous because it can precisely deliver a liquid and measure its flow rate over a wide range of flow rates. The range of flow rates which can be measured accurately range from the low rates often used for IV administration to the high rates administered by IV during, for example, surgical proceedings.

The subject invention is an IV administration set-up that includes a main flow line having a capped spike for receiving an IV bag at the top end thereof and an airless, dripless, fluid monitoring chamber positioned in the flow line such that the single flow line can deliver fluids across a wide range of flow rates, including high flow rates, without the risk of air embolism. In alternative embodiments, there are a variety of fluid pathways or flow limbs diverging from the main flow line which then merge together at the bottom, permitting the injection of fluids into a patient over a wide range of flow rates. Optionally, there may be a plurality of capped spikes each having its own line which then merges into the main flow line, thus allowing administration of a variety of fluids at one time. In a preferred embodiment, the main flow line diverges downwardly into a first flow line having a monitoring chamber mounted therein which is capable of administering fluids at a first flow rate. A shunt line is placed in the main flow line which bypasses the first flow line and its monitoring chamber. A flow monitoring chamber is also mounted in the shunt line, and is capable of administering fluids at a second flow rate. In a preferred embodiment, the first flow line and the shunt line diverge from the main flow line at a valve which can direct fluid flow preferentially to the first flow line or the shunt line or both. In this regard the valve is a "three-way" valve. As an alternative to the three-way valve, clips and/or clamps of the type widely used in the medical arts can be used to selectively open and close the lines to route IV fluids through a selected one or both of the two available fluid monitoring chambers. In the preferred embodiment, the first flow line is used for administering fluids at low-flow rates; while the shunt line is used for administering fluids at high-flow rates. Henceforth, the first flow line will be referred to as the "low-flow limb", while the shunt line will be referred to as the "high-flow limb." In one embodiment of the subject invention, the fluid monitoring chambers of both the low-flow limb and the high-flow limb are airless, dripless chambers comprising the novel flow meter described herein. Alternatively, the fluid monitoring chamber of the low-flow limb comprises a drip chamber of the type well known and widely used in the art, while the fluid monitoring chamber of the high-flow limb remains airless and dripless. In some embodiments, the flow meter of the high-flow limb can be replaced with a simple flow indicator, such as an impeller which merely indicates that fluid flow is occurring without measuring its rate. In such embodiments, it is desirable that the tubing sections constituting the high-flow limb be proportionately sized relative to those of the low-flow limb such that fluid flow in the high-flow limb can be calculated as a multiple of the low flow rate. Then, to monitor high-flow rate, both limbs are opened, the impeller indicates flow in the high-flow limb, and its rate can be determined by counting the drip rate in the low-flow limb and applying the appropriate multiplier; for example, the rate could be 10 times or 100 times the low-flow rate. As an alternative to the impeller, a deflector could be mounted in the airless, dripless, fluid monitoring chamber of the high-flow limb, which, by its deflection, indicates flow. Additionally, should flow rate be desired to be monitored, appropriate indicia such as a scale or calibrations could be provided which allow one to take readings of the degree of deflection and thereby read the rate of flow off of the scale. In any embodiment of the subject invention, the high-flow limb lacks a drip chamber, and thus eliminates the possibility of air embolism.

The flow meter of the subject invention comprises a member which is capable of elastic displacement along a longitudinal axis when subjected to a force along that axis. As used according to the subject invention, the force is supplied by the fluid flow. Advantageously, the displacement member comprises a portion which is displaced in response to even small forces, such as are encountered in slow drip administration, as well as other portions which are not displaced in response to small forces but are displaced when subjected to greater forces. In a preferred embodiment, the displaceable member comprises a continuous gradient of displacement resistance.

In a preferred embodiment, the displaceable member is extendable in response to force, and is retracted in its relaxed position. The extendable member of the subject invention is disposed within a tube which carries the IV fluid as it is being delivered. As the fluid moves past the extendable member, the member is subjected to a longitudinal force. At low flow rates the portion of the member which responds to small forces will become extended to an extent which is proportional to the flow rate. This permits accurate measurement of low flow rates. As flow rate increases, more and more resistant portions will extend in response to the increased force, proportional to flow rate.

The flow meter of the subject invention is not restricted in its use to just the two-limb IV apparatus described herein, but can be used in an IV set-up having a single limb or flow path. Further, various embodiments of the subject flow meter can be used in any fluid flow path of any type where flow rate is desired to be measured. Finally, a novel type of displaceable member or spring is described which is characterized by either a continuous or a variable gradient of displacement resistance capacity across its length, depending on the embodiment desired. While use of the novel displaceable member is exemplified in the flow meter of the subject invention, its use in a variety of different applications will be immediately clear to the skilled artisan.

BRIEF DESCRIPTION OF THE DRAWINGS

For a better understanding of these and other objects of the present invention, reference will be made to the following detailed description of the invention which is to be read in conjunction with the following drawings, wherein.

DETAILED DESCRIPTION OF THE INVENTION

Figure 1:
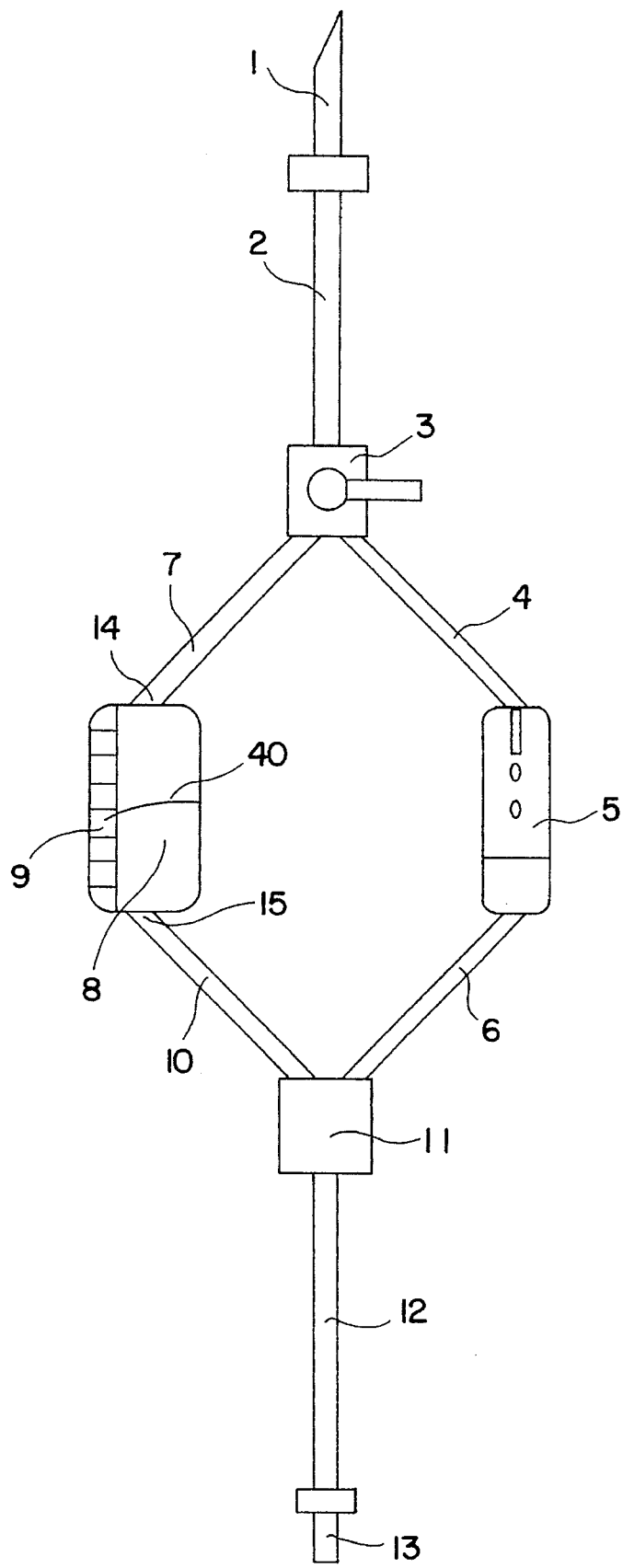
FIG. 1 depicts a preferred embodiment of a two-limb IV apparatus of the subject invention.

In a typical system for intravenous administration of liquid to a patient, the liquid to be administered is initially contained within a storage reservoir, which is commonly made of a limp, flexible material such as a flexible synthetic plastic. In a gravity flow system, the storage bag is conveniently suspended on a hook which extends from a pole or a stand supported on the floor by a base in order to inhibit tipping over of the pole. The storage bag, when hanging from such a hook, has a downwardly facing mouth to which an IV administration set is attached, most commonly by means of an IV "spike". With reference to the drawings, FIG. 1 illustrates an embodiment of the IV set of the present invention having a main flow line 2 that is made up of at least one tubing section, and the top end of which is equipped with a capped spike 1 of conventional design that is capable of penetrating the mouth of a typical IV fluid storage bag, thereby enabling the fluid contained in the storage bag to freely enter the main flow line and down the fluid flow path through the IV set. In the typical set-up, as described above, the fluid storage bag is suspended from a suitable hanger. Once the spike 1 has been inserted into the bag, IV fluids contained therein can flow under the influence of gravity downwardly through the fluid flow path. In the preferred embodiment of the subject invention, fluid flowing downward through the fluid flow path encounters a three-way valve 3 which serves to direct the fluid either through a high-flow limb 7 or a low-flow limb 4, or both. Alternatively, the three-way valve 3 can be replaced by a simple Y-connector which allows the main flow line 2 to branch into high-flow limb 7 and low-flow limb 4, with clips or clamps being used to permit or prevent fluid flow through either or both of the limbs. Alternatively, a two-way valve could replace the Y-connector and could thereby serve to direct the fluid through either of flow limbs 4 or 7. A standard drip chamber 5 is mounted in the low-flow limb 4 that serves to regulate and permit monitoring of the rate of fluid flow that can pass through the line and thus be administered to the patient. Drip chamber 5 is employed to administer IV fluids to the patient at a relatively low flow rate continuously over a long period of time. For example, if the IV set is for a child, such rates might be 4 ml/Kg/H up to 10 Kg, and 6 ml/Kg/H for children 10–20 Kg. Fluid flows out of drip chamber 5 via tubing section 6 which is connected to a Y-connector 11, which in turn serves to direct fluid from tubing section 6 and into tubing section 12, which, in the preferred embodiment, is approximately the same inside diameter as is the tubing section which makes up main flow line 2. Tubing section 12 terminates in male connecter 13 which is a standard connector of the type well known in the art through which fluid passes into a catheter or needle for intravenous administration to the patient.

Also connected to three-way valve 3 in the preferred embodiment, or connected to the optional Y-connector or two-way valve that replaces three-way valve 3 in alternative embodiments, is high-flow limb 7, which comprises a tubing section having an inside diameter larger than that of the low-flow limb 4 and of sufficient diameter to permit flow rates required for volume resuscitation (for example>1 L/min. for adults). A high-flow airless chamber 8 is mounted in main flow line 7 and comprises the flow meter of the subject invention in its preferred embodiment. Alternatively, and as depicted in FIG. 1, the flow meter can be replaced in chamber 8 with a simple deflector 40 which will, by deflection, indicate flow. In some embodiments chamber 8 also comprises indicia such as a scaled series of gradations or calibrations 9 which, in concert with deflector 40, enables one to take readings that indicate flow rate by the degree of deflection of deflector 40. These indicia can be color-coded so as to correspond to the colored zones of a Broselow tape, well known to those skilled in the art as providing a means for rapidly determining proper flow rate for children. The flow meter of the high-flow airless chamber has an ingress aperture 14 for fluid inflow and an egress aperture 15 for fluid outflow. Egress aperture 15 is connected to the upper end of tubing section 10, while the lower end of tubing section 10 is connected to the second arm of Y-connecter 11, such that fluid flowing through high-flow limb 7 and through high-flow airless chamber 8 downward through tubing section 10, flows through Y-connector 11 and into tubing section 12, and then ultimately through male connector 13 and onward into the patient. As is apparent from this disclosure, the high-flow limb can be employed in the present system to rapidly infuse blood or selected medications into a patient without having to replace or disconnect the IV set-up.

Figure 2:
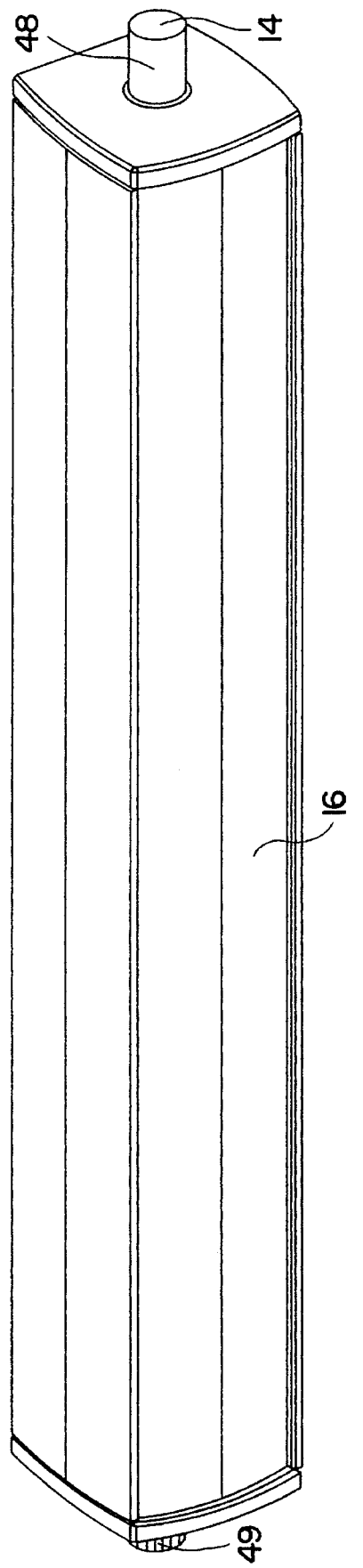
FIG. 2 depicts an embodiment of the flow meter of the subject invention.
Figure 3:
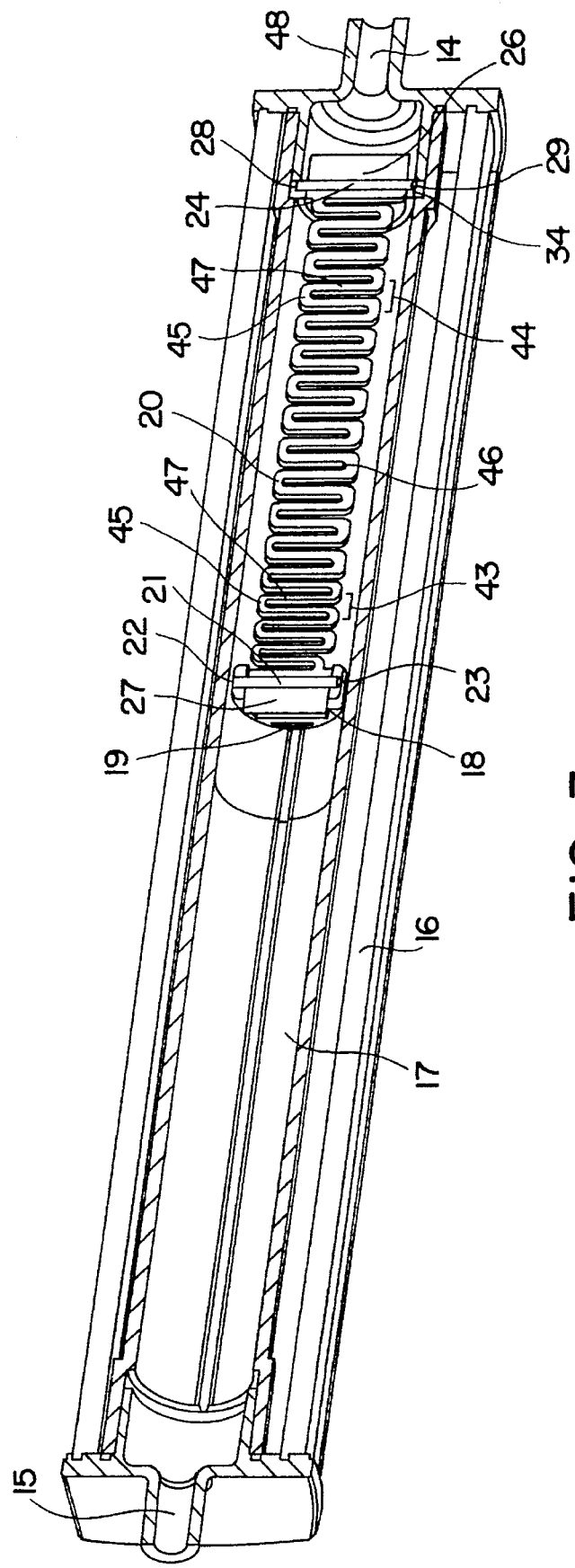
FIG. 3 depicts a lengthwise cross-sectional view of a preferred embodiment of the subject flow meter.

Referring now to FIGS. 2 and 3, the flow meter of the subject invention can easily be described to those skilled in the art. In a preferred embodiment the flow meter of the subject invention comprises an elongated housing 16 having a fluid ingress aperture 14 at one end and a fluid egress aperture 15 at the other, as well as a fluid flow-through passage defined by internal surface 17 such that the fluid to be monitored flows in ingress aperture 14 through the fluid flow-through passage defined by internal surface 17 and out through fluid egress aperture 15. In the preferred embodiment internal surface 17 defines a substantially cylindrical fluid flow-through passage, but there is no reason why alternative shapes would not suffice as well.

Affixed proximal to ingress aperture 14 in the interior of housing 16 is elastic displaceable member 20 having a first end 26 and a second end 27. Displaceable member 20 has its first end 26 affixed proximally to ingress aperture 14 by retaining pin 24 in the preferred embodiment. In this embodiment, retaining pin 24 passes through first end 26 extending slightly beyond each side of first end 26 and into retaining slots 28 and 29 which are positioned proximal to ingress aperture 14 such that when displaceable member 20 is affixed in place, it is positioned in the fluid flow-through passage defined by internal surface 17. In a preferred embodiment, displaceable member 20 is constructed such that it comprises a continuous gradient of displacement resistance capacity across its length from its first end 26 to its second end 27. Alternatively, the displaceable member 20 can be manufactured to possess a variable gradient of displacement resistance such that different "zones" of the displaceable member have different displacement resistance characteristics. The displaceable member, in a preferred embodiment, comprises a plurality of loops, exemplified by loops 43 and 44, each of which comprises a crest 45, a trough 46, and two connectors 47 which serve to connect crests 45 to troughs 46. In the preferred embodiment, displaceable member 20 comprises a plurality of loops interconnected so as to resemble a compressed sine wave, as is most clearly depicted in FIG. 3. The gradient of displacement resistance across displaceable member 20 is accomplished by manufacturing the constituent loops to be of different width, diameter, or separation, or a combination of those factors. For example, loop 43 is depicted as proximal to second end 27, and in the depicted embodiment accordingly has a resistance of displacement that is less than that of loop 44, which is proximal to first end 26. It can easily be seen that the diameter of the material forming crest 45, trough 46, and connectors 47 of loop 43 is less than the diameter of the material making up the corresponding components of loop 44. As such, less force is required to displace that portion of displaceable member 20 represented by loop 43 than is required to displace that portion of displaceable member 20 represented by loop 44. From this description it will be obvious to the skilled artisan that there is an almost infinite number of different configurations for displaceable member 20 based upon variations in width, diameter, separation, or any combination of those factors, which can result in varying displacement resistance capacity across the length of displaceable member 20. In the most preferred embodiment, the displacement resistance of displaceable member 20 is greatest proximal to its first end 26 and is gradually decreasing until the least resistance is encountered proximal to second end 27, and is thus oriented in the preferred embodiment such that that portion of displaceable member 20 having the least displacement resistance is farthest away from ingress aperture 14. Optionally, however, this orientation may be reversed.

Alternatively, taking advantage of the variable levels of displacement resistance capability just described, the skilled artisan could construct the displaceable member as a compressible member which is fully extended in its relaxed position and has a continuous gradient, or varying zones, of compression resistance. In a preferred embodiment of this alternative form of displaceable member, the member is oriented within housing 16 such that that portion of the member having the least compression displacement resistance would be closest to ingress aperture 14, and that position having the greatest compression displacement resistance would be proximal to egress aperture 15.

In practice, the most preferred embodiment of the subject invention must be constructed such that housing 16 is of sufficient length to allow complete displacement of displaceable member 20 such that at its full extension, second end 27 does not reach the end of housing 16 proximal to egress aperture 15. In operation, as fluid flows into ingress aperture 14 and through the fluid flow-through passage defined by internal surface 17, the fluid passes over, around and through displaceable member 20, thereby exerting force which causes displacement of displaceable member 20 toward egress aperture 15 through which fluid flows out of the subject flow meter. It will of course be understood that the degree of movement of displaceable member 20 is determined by the rate of flow of fluid through the flow meter. The greater the flow rate, the greater the displacement of displaceable member 20, as is fully understood by anyone skilled in the art.

In a preferred embodiment, a piston 18 is attached to second end 27 of displaceable member 20. As the fluid flows through a preferred embodiment of the subject flow meter, it encounters piston 18, which, in the preferred embodiment, comprises at least one, and preferably a plurality, of flow-through apertures 19, which allow the fluid to pass through the piston 18. As the fluid encounters piston 18 and flows through fluid apertures 19, the force of the fluid tends to displace piston 18 away from ingress aperture 14 and toward egress aperture 15.

The external surfaces of the subject flow meter are ideally primarily constructed from transparent or translucent materials, preferably plastics, and a scale or indicator strip having graduations thereon is affixed to or molded into housing 16 such that an observer can take readings of the degree of displacement of displaceable member 20 as fluid is flowing through the flow meter. The graduations are such that displaceable member 20 is in the zero position when no fluid is flowing through the flow meter. Piston 18 and displaceable member 20 are preferably made of non-translucent material to provide contrast which facilitates the taking of displacement readings.

Figure 4:
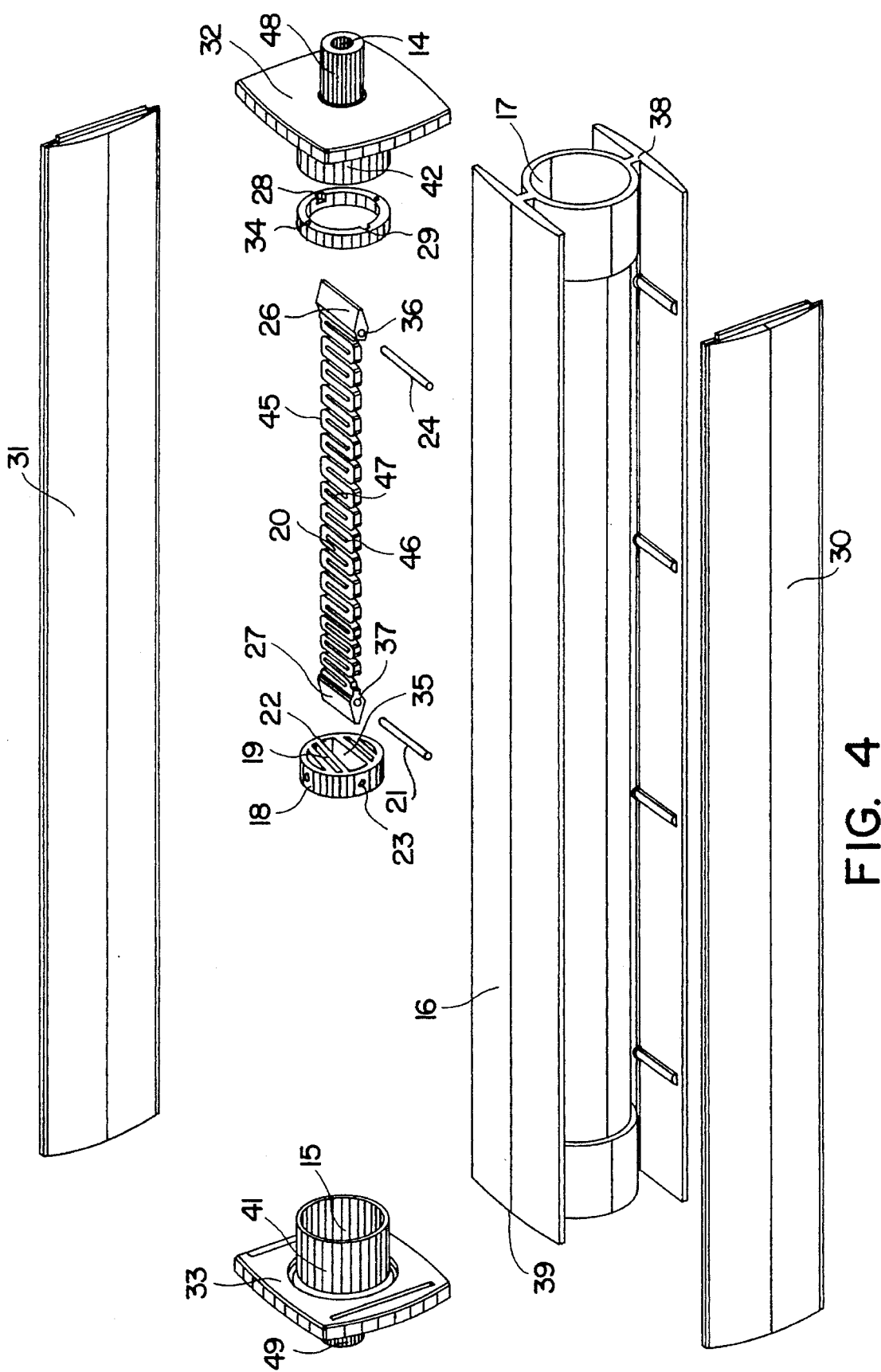
FIG. 4 is an exploded view of the most preferred embodiment of the subject flow meter.

With reference to FIG. 4, one can see that assembly of the most preferred embodiment of the subject flow meter is a simple matter. Ingress end cap 32 has an external surface and an internal surface with ingress aperture 14 extending completely therethrough. In the most preferred embodiment, there is a projection 48 which serves as a male connector, and which defines the ingress aperture 14 on the external surface of ingress end cap 32, which is complementary in size to the inside diameter of the tubing section making up high-flow limb 7. In this embodiment on the internal surface of ingress end cap 32 ingress aperture 14 is surrounded by a projection 42 having a external surface which is complementary to internal surface of 17 of housing 16. Similarly, egress end cap 33 has an external surface and an internal surface with egress aperture 15 extending therethrough. On the external surface of egress end cap 33, egress aperture 15 is defined by a projection 49 serving as a male connector and having an external diameter complementary in size to the internal diameter of highflow limb tubing section 10. On the internal surface of egress end cap 33, there is a projection 41 surrounding egress aperture 15 having an external surface which is complementary to the internal surface 17 of housing 16.

To assemble, retaining ring 34 is slipped over first end 26 of displaceable member 20 such that first end 26 completely extends therethrough. Retaining pin 24 is then inserted through pin receiving orifice 36 which extends breadthwise through first end 26. Properly positioned, the ends of retaining pin 24 extend slightly beyond the sides of first end 26. Retaining ring 34 is then moved back towards first end 26 such that the ends of retaining pin 24 which extend beyond each side of first end 26 are received in receiving slots 28 and 29. Retaining ring 34 is then affixed to the internal surface of ingress end cap 32 in a position complimentary to ingress aperture 14 which extends through ingress end cap 32. Next, second end 27 is inserted through receiving aperture 35 of piston 18. In the most preferred embodiment, receiving aperture 35 serves not only to receive second end 27 but also acts as a flowthrough aperture in piston 18 similar to flow-through apertures 19. When properly positioned for assembly, second end 27 is aligned in receiving aperture 35 such that retaining pin 21 can be inserted through pin receiving aperture 23 into pin receiving orifice 37 extending breadth wise through second end 27 and exiting pin receiving aperture 22. When properly assembled, the ends of retaining pin 21 extend beyond the sides of second end 27 and into pin receiving apertures 23 and 22, but not substantially beyond the external surface of piston 18. Piston 18 is thusly affixed to second end 27 of displaceable member 20.

During assembly of the subject flow meter egress end cap 33 is affixed to housing 16 such that the internal surface of egress end cap 33 is affixed complementary to egress end 39 of housing 16. In the most preferred embodiment, side panels 30 and 31 are made of transparent plastic, and are configured so as to act as lenses which magnify or otherwise aid in one's ability to observe the position of piston 18 and displaceable member 20 within the flow meter when the flow meter is in operation. Side panels 30 and 31 are affixed to housing 16 and egress end cap 33. Finally, the entire assembly comprising piston 18, displaceable member 20, retaining ring 34 and ingress end cap 32 can then be lowered, piston-end first, into the fluid flow through passage defined by internal surface 17 of housing 16 such that the internal surface of ingress end cap 32 ultimately contacts the ingress end 38 of housing 16, where it is affixed to housing 16.

In operation, this embodiment of the subject flow meter receives IV fluid through ingress aperture 14, and the fluid passes over displaceable member 20 through apertures 35 and 19 of piston 18, through the remainder of the fluid flow passage and out egress aperture 15. As the fluid flows through the flow meter it exerts force upon piston 18 and displaceable member 20, thereby causing the extension of displaceable member 20 as piston 18 is forced towards egress aperture 15. An observer monitoring the fluid flow rate can determine the location of piston 18 by looking through housing 16, or preferably side panels 30 or 31, and optionally can take readings off a scale or other indicator which is properly calibrated and affixed to the subject flow meter.

All elements of the subject invention which have been described as "tubing sections" are preferably medical grade, resilient, flexible plastic tubing as is well known in the art. The preferred embodiments of the flow meter of this invention have a housing 16 which is made of a transparent material, such as suitable plastic. In the preferred embodiments, interior surface 17 is substantially cylindrical and extends throughout the length of housing 16, defining a fluid flow-through passage extending between ingress aperture 14 and egress aperture 15 such that all are in fluid flow communication. The preferred embodiments of the displaceable member are constructed from known elastomeric materials, especially natural or synthetic rubber-like materials that are easily molded into the desired configuration using well-known manufacturing techniques. Optionally, the displaceable member could be manufactured from metals suitable for extrusion and other known wire forming and configuring techniques.

Those skilled in the medical arts and the art of biomedical devices, as well as other arts where measurement of fluid flow rates is useful, will readily perceive various other useful applications for the flow meter of the present invention and various ways in which such devices can be incorporated into conventional and state of the art biomedical or other fluid systems.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An intravenous fluid administration apparatus comprising a main flow line; an airless, dripless, fluid monitoring chamber positioned in said flow line such that fluid flowing through said flow line will pass through said airless, dripless, fluid monitoring chamber; a flow indicator disposed within said airless, dripless, fluid monitoring chamber such that when fluid flows through said chamber said flow indicator evidences fluid flow; and wherein said main flow line diverges into at least two flow limbs, at least one of said limbs being a low-flow limb and at least one of said limbs being a high-flow limb; and wherein said airless, dripless, fluid monitoring chamber is positioned such that fluid flowing through the main flow line and down through said high-flow limb will pass through said airless, dripless, fluid monitoring chamber.

2. The intravenous fluid administration apparatus of claim 2, wherein said flow indicator is an impeller.

3. The intravenous fluid administration apparatus of claim 2, wherein said flow indicator is a deflector.

4. The intravenous fluid administration apparatus of claim 3, wherein said fluid monitoring chamber comprises indicia for determining fluid flow rate.

5. The intravenous fluid administration apparatus of claim 1, wherein said flow indicator is a flow meter comprising a displaceable member having a longitudinal axis, said member capable of elastic displacement along said longitudinal axis when subjected to a force along that axis.

6. The intravenous fluid administration apparatus of claim 5, wherein said displaceable member comprises a continuous gradient of displacement resistance.

7. The intravenous fluid administration apparatus of claim 6, wherein said displaceable member comprises a continuous gradient of displacement resistance such that a portion of said member is displaced when subjected to small forces, and another portion of said member is displaced only when subjected to greater forces.

8. The intravenous fluid administration apparatus of claim 7, wherein said flow meter further comprises indicia for determining fluid flow rate arranged in said flow meter such that as fluid flows therethrough, subjecting said displaceable member to forces which cause displacement of said member, readings can be taken from the relative positions of said member and said indicia which indicate fluid flow rate.

9. The intravenous fluid administration apparatus of claim 8, wherein said indicia consist of calibrations.

10. The intravenous fluid administration apparatus of claim 8, wherein said indicia are color-coded, and correspond to the colored zones of a Broselow tape.

11. The intravenous flow administration apparatus of claim 1, wherein said low-flow limb comprises a drip chamber, and wherein the rate of fluid flow through said high-flow limb is calculated by counting the drip ram in said drip chamber of said low-flow limb and applying a predetermined multiplier.

12. A flow meter comprising an elongated housing having an internal surface and an external surface, and having first and second ends a longitudinal axis passing through said ends; said first end having an ingress aperture therethrough and said second end having an egress aperture therethrough such that said internal surface and said ingress and egress apertures define a fluid flow-through passage through said housing; an elastic displaceable member having a first end and a second end, a longitudinal axis passing through said ends, and comprising a variety of displacement resistance capacity across its length from said first end to said second end; said displaceable member being affixed within said housing the length of displaceable member parallel with the longitudinal axis of the housing such that as fluid flows through said fluid flow-through passage in said housing the fluid contacts said displaceable member, which is then displaced along said longitudinal axis of said member by the forces exerted upon it by the fluid flow.

13. The flow meter of claim 12, wherein said displaceable member comprises a continuous gradient of displacement resistance capacity across its length from said first end to said second end.

14. The flow meter of claim 13, wherein said displaceable member is affixed proximal to said ingress aperture such that the end of said displaceable member having the greatest displacement resistance capacity is closer to said ingress aperture than to said egress aperture.

15. The flow meter of claim 14, wherein said displaceable member is retracted in its relaxed position, and is extended as it is displaced when subjected to fluid flow force.

16. The flow meter of claim 13, wherein said displaceable member is affixed proximal to said egress aperture such that the end of said displaceable member having the greatest displacement resistance capacity is closer to said egress aperture than to said ingress aperture.

17. The flow meter of claim 16, wherein said displaceable member is extended in its relaxed position and is contracted as it is displaced when subjected to fluid flow force.

18. An elastic displaceable member made of an elastomeric material having two ends, a longitudinal axis extending through said ends, and comprising a plurality of coplanar loops disposed along said axis and between said ends, said loops having different capacities of displacement resistance and connected one to another such that when said member is subjected to force along said axis, said loops cause said member to display a variety of displacement resistance capacity across its length along said axis from one end to the other.

19. The elastic displaceable member of claim 18, wherein said loops are connected one to another in a configuration such that said variety of displacement resistance capacity is arranged as a continuous gradient from least resistant to most resistant.

20. The elastic displaceable member of claim 18, wherein the displacement resistance capacity of said loops is a function of the diameter of the material from which said loops are made.

21. The elastic displaceable member of claim 18 wherein the displacement resistance capacity of said loops is a function of the size of said loops and wherein a plurality of said loops are differently sized one from another.

* * * * *

UNITED STATES PATENT AND TRADEMARK OFFICE
CERTIFICATE OF CORRECTION

Page 1 of 2

PATENT NO. : 5,599,303

DATED : February 4, 1997

INVENTOR(S) : Richard Melker, Eric J. Huisman, Brad D. Wellington

It is certified that error appears in the above-identifie d patent and that said Letters Patent is hereby corrected as shown below:

Column 2: Line 42: "In fight" should read --In light--; Lines 63-64: "envisions two drip chambers: no chamber is "dripless"." should read --envisions two drip chambers: no chamber is "dripless"--.

Column 3: Line 11: "fife-threatening" should read --life-threatening--.

Column 7: Line 29: "most dearly" should read --most clearly--.

Column 8: Line 61: "highflow limb" should read --high-flow limb--.

Column 9: Line 14: "flowthrough" should read --flow-through--.

UNITED STATES PATENT AND TRADEMARK OFFICE
CERTIFICATE OF CORRECTION

Page 2 of 2

PATENT NO. : 5,599,303

DATED : February 4, 1997

INVENTOR(S) : Richard Melker, Eric J. Hulsman, Brad D. Wellington

It is certified that error appears in the above-identifie d patent and that said Letters Patent is hereby corrected as shown below:

Column 10: Line 36: Claim 2: "apparatus of claim 2," should read --apparatus of claim 1,--.

Line 38, Claim 3: "apparatus of claim 2," should read --apparatus of claim 1,"

Column 11: Line 4: "drip ram" should read --drip rate--.

Signed and Sealed this

Eighth Day of July, 1997

*Attest:*

BRUCE LEHMAN

*Attesting Officer*  Commissioner of Patents and Trademarks